United States Patent [19]

Fujimoto et al.

[11] Patent Number: 5,130,024
[45] Date of Patent: Jul. 14, 1992

[54] HYDROPHILIC POROUS FLUOROPOLYMER MEMBRANE

[75] Inventors: Hiroyoshi Fujimoto; Mari Sakai; Katsuhiko Morishita; Kazuya Morimoto, all of Okayama, Japan

[73] Assignee: Japan Gore-Tex, Inc., Tokyo, Japan

[21] Appl. No.: 726,599

[22] Filed: Jul. 8, 1991

Related U.S. Application Data

[63] Continuation-in-part of Ser. No. 634,892, Dec. 27, 1990, abandoned.

[30] Foreign Application Priority Data

May 18, 1990 [JP] Japan .................. 2-128677

[51] Int. Cl.⁵ .............................. B01D 71/36
[52] U.S. Cl. .................. 210/500.36; 526/255
[58] Field of Search ............ 210/500.36, 500.27, 210/500.21; 526/250, 255

[56] References Cited

FOREIGN PATENT DOCUMENTS

| | | |
|---|---|---|
| 0054354 | 11/1981 | European Pat. Off. . |
| 0071170 | 7/1982 | European Pat. Off. . |
| 0190558 | 1/1986 | European Pat. Off. . |
| 0203459 | 5/1986 | European Pat. Off. . |
| 0326360 | 1/1989 | European Pat. Off. . |

*Primary Examiner*—Frank Sever
*Attorney, Agent, or Firm*—Gary A. Samuels

[57] ABSTRACT

The present invention provides porous hydrophilic fluoropolymer membranes whose pores are coated with a hydrophilic fluorine-containing copolymer that provides durable hydrophilic properties to the membrane.

29 Claims, No Drawings

HYDROPHILIC POROUS FLUOROPOLYMER MEMBRANE

CROSS-REFERENCE TO RELATED APPLICATIONS

This application is a continuation-in-part of application Ser. No. 07/634,892 filed Dec. 27, 1990, abandoned.

FIELD OF THE INVENTION

This invention relates to porous fluoropolymer membranes that are hydrophilic; and more particularly to fluoropolymer membranes having continuous pores through the membrane in which the inner surface of the pores are coated with a hydrophilic fluorine-containing copolymer.

BACKGROUND OF THE INVENTION

Porous fluoropolymer membranes having a large number of continuous fine pores are known. Such materials have been extensively employed as filters because of the fact that fluoropolymers, and particularly polytetrafluoroethylene (PTFE) are known to have high heat resistance and chemical resistance. However, they cannot be applied to separation of particles dispersed in water due to their high liquid water repellency and low liquid water permeability. In other words, they are hydrophobic in nature. In order to provide such hydrophobic porous fluorine membranes with a capability of permeating water therethrough, it is necessary to make inner surfaces of the fine pores of the materials hydrophilic. Review has been made of various methods for making the inner surface of the fine pores of the porous fluoropolymer membrane hydrophilic. Such methods may include, for example, (1) the method of replacement with water after impregnation of the membrane with a hydrophilic organic solvent such as an alcohol; (2) the method of impregnating the membrane with a surfactant through its alcohol solution; (3) the method of impregnating the membrane with a monomer containing a hydrophilic group and then polymerizing the monomer; (4) the method of making the membrane hydrophilic by impregnation with a hydrophilic polymer such as polyvinyl alcohol through its aqueous solvent solution; (5) the method of impregnating the membrane with a monomer containing a hydrophilic group and then graft-polymerizing the monomer by treatment with strong reducing agents or plasma gases, or by irradiation of high energy radiation such as a gamma ray, an electron beam, etc. These conventional methods, however, have various drawbacks. The method (1) has the problem that the effect of replacement with water is lost once the materials have been dried. The method (2) has the drawback that the surfactant may likely elute thereby worsening durability. The methods (3) and (4) may have the likelihood to clog up the fine pores of the materials and have the drawback that the polymer may be likely to elute and their durabilities are poor. Consequently, the cross-linking or crystallizing treatments of the impregnated polymer of the surfactant are sometimes carried out for the propose of the preventing of the elution of the polymer in the methods (2), (3) and (4). These treatments are described in examined Japanese Patent Publication Nos. 21270/1978, 8869/1979. 154737/1981 and 98640/1989. The method (5) may deteriorate the mechanical properties of the materials and it may be difficult to prevent homopolymerization of the monomer and the elution of the homopolymer.

SUMMARY OF THE INVENTION

The present invention overcomes the deficiencies of the above-described products and procedures. The present invention provides porous hydrophilic fluoropolymer membranes whose pores are coated with a hydrophilic fluorine-containing copolymer that provides durable hydrophilic properties to the membrane simply by the impregnation treatment of the copolymer without any special treatment.

More specifically, this invention is directed to a hydrophilic porous membrane comprising a fluoropolymer membrane having continuous pores through the membrane, in which at least a portion of the interior of the membrane is coated with a hydrophilic fluorine-containing copolymer comprising (i) units of a fluorine-containing monomer and (ii) units of a non-fluorinated vinyl monomer containing a hydrophilic functional group;

wherein the amount of the copolymer present is sufficient to impart increased hydrophilicity to the fluoropolymer membrane.

Preferably, the fluorine content of the hydrophilic fluorine-containing copolymer is between 2 and 60 percent by weight of the copolymer.

Preferably, also, the ratio of the formula weight of the recurring units of the copolymers to the number of functional group units in the formula is between 45 and 700.

DESCRIPTION OF THE INVENTION

In accordance with the present invention, as long as continuous pores are present in the porous fluoropolymer membrane to be used as a substrate, the method for forming such pores is not restricted to a particular method. For example, stretching, i.e., expanding, or bubbling, or extraction, or the like may be used.

The kind of fluorine resin used to make the fluoropolymer membrane is not restricted and a variety of fluorine resins may be used. While the fluorine resin preferably used as the membrane for the present invention is polytetrafluoroethylene; in addition, tetrafluoroethylene/hexafluoropropylene copolymer, polyvinylfluoride, polyvinylidene fluoride, and the like, may also be used. Porous polytetrafluoroethylene is preferred, especially a porous expanded polytetrafluoroethylene.

The porous fluoropolymer membrane preferably used as a substrate for the present invention is comprised of expanded polytetrafluoroethylene having a porosity ranging usually from 15% to 95%, preferably from 50% to 95% and a pore diameter ranging usually form 0.02 to 30 microns, preferably from 0.02 to 10 microns. This substrate is described in examined Japanese Patent Publication Nos. 45,773/1981 and 17,216/1981, and in U.S. Pat. No. 4,187,390.

The hydrophilic fluorine-containing copolymer used to coat the inner surfaces of the fine pores of the porous fluoropolymer membrane may be a copolymer of a fluorine-containing ethylenically unsaturated monomer and a non-fluorinated vinyl monomer containing a hydrophilic group. It may be made by copolymerizing the monomers.

Preferably the fluorine-containing monomer of the fluorine-containing copolymer will be a vinyl monomer such as, for example, tetrafluoroethylene, vinyl fluoride, vinylidene fluoride, monochloro-trifluorethylene, dichlorodifluoroethylene, hexafluoropropylene, and the like.

More preferably, the fluorine-containing vinyl monomer can be described as $$CXY=CFZ$$

wherein Z can be fluorine or hydrogen and X and Y can each be selected from hydrogen, fluorine, chlorine and —$CG_3$.

Other desirable fluorine-containing monomers useful herein include:

$$CH_2=CR$$
$$|$$
$$COORf$$

$$CH_2=CR$$
$$|$$
$$OCORf$$

$$CH_2=CR$$
$$|$$
$$O=C-Rf$$

$$CH_2=CR$$
$$|$$
$$O-Rf$$

$$CH_2=CR$$
$$|$$
$$CONHRf$$

In the above formulae, R is hydrogen, fluorine, a methyl group, an ethyl group, a trifluoroethyl group ($CF_3$), or pentafluoroethyl ($C_2F_5$). Rf is a perfluoroalkyl group with four to 21 carbons.

Meanwhile, examples of monomers that contain hydrophilic groups include those that have hydroxyl groups, carboxyl groups, sulfone groups, phosphoric acid groups, amide groups that may be N-substituted, and amino groups that may be N-substituted. Monomers in which an alkylene oxide such as ethylene oxide or propylene oxide has been subjected to an additional reaction with the active hydrogen in these groups are also favorable. Those that yield copolymers containing hydrophilic groups by performing first copolymerization and then hydrolysis, such as vinyl acetate, are also used.

Specific examples of these hydrophilic monomers include vinyl alcohol, acrylic acid, methacrylic acid, and other such unsaturated carboxylic acids, as well as alkylene oxide adducts of acrylic acid or methacrylic acid, such as those shown below.

$$CH_2=CR \quad (7)$$
$$|$$
$$COO(C_2H_4O)nH$$

$$CH_2=CR \quad (8)$$
$$|$$
$$COO(C_3H_6O)nH$$

$$CH_2=CR \quad (9)$$
$$|$$
$$COO(C_3H_6O)m(CF_2H_4O)nH$$

$$CH_2=CR \quad (10)$$
$$|$$
$$CONH(CH_2)_3NH_2$$

In the above formulae, R is hydrogen or a methyl group and n and m are integers greater than or equal to one and preferably one to twenty.

Both the fluorine-containing monomer and the monomer containing hydrophilic groups may be used singly or in combinations of two or more types. And if needed, other vinyl monomers, such as alkyl esters or acrylic acid or methacrylic acid, esters of trimethylol propane or other such polyhydric alcohol and acrylic acid or methacrylic acid, and the like can also be used jointly with the above-mentioned fluorine-containing monomer and the monomer containing hydrophilic groups.

The copolymer of vinyl alcohol with the fluorine-containing monomer may be prepared by saponifying a copolymer of vinyl acetate with the fluorine-containing monomer to thereby convert the acetate group contained in the copolymer into the hydroxyl group. In this case, all of the acetate groups contained in the copolymer are not necessarily replaced by the hydroxyl group and the conversion of the acetate groups into the hydroxyl groups may be carried out to the extend needed to provide the copolymer with hydrophilic properties.

The fluorine content of the fluorine-containing hydrophilic copolymer to be used in the present invention may range usually form 2% to 60%, preferably form 10% to 60%, and most preferably 20%–60% on a weight basis. If the fluorine content of the fluorine-containing hydrophilic copolymer becomes too high, on the one hand, the hydrophilic properties of the polymer may be lessened, though the heat resistance becomes better. If the fluorine content becomes too low, on the other hand, adhesion of the fluorine-containing hydrophilic polymer to the porous fluoropolymer membrane may be reduced and the heat resistance may be decreased.

The equivalent weight is the formula weight divided by the number of functional units int eh formula and will be generally between 45 and 700, preferably, 60-500 and most preferably, 60–450.

If the equivalent weight is lower than 45, the water solubility of the fluorine-containing hydrophilic copolymer may be too high and the fluorine-containing copolymer will elute away with water; and if the equivalent weight is higher than 700, the hydrophilic properties will be lessened, but he interaction between the copolymer and the porous membrane will be increased and thus the copolymer will not tend to elute away.

The following Table provides the mole % fluorine monomer units in the copolymer, the fluorine weight % (F-wt %) and the equivalent weight (EqW) for a number of copolymers (where VOH is vinyl alcohol):

| Copolymer | Molar Ratio in Copolymer | Mole % of F-monomer Units in copolymer | F-wt % | Eq-W |
|---|---|---|---|---|
| $(CF_2=CF_2)_x/(VOH)_y$ | x = 1, y = 40 | 2.4 | 4.2 | 45.5 |
| | 1, 30 | 3.2 | 5.5 | 46.4 |
| | 1, 20 | 4.8 | 7.9 | 48.0 |

-continued

| Copolymer | Molar Ratio in Copolymer | | Mole % of F-monomer Units in copolymer | F-wt % | Eq-W |
|---|---|---|---|---|---|
| | 1, | 10 | 9.1 | 14.3 | 53 |
| | 1, | 4 | 20 | 27.5 | 68 |
| | 1, | 1 | 50 | 53.1 | 143 |
| | ,10, | 1 | 91 | 72.8 | 1043 |
| $(CF_2 = CH_2)_x/(VOH)_y$ | $x = 1,$ | $y = 40$ | 2.4 | 2.1 | 44.6 |
| | 1, | 30 | 3.2 | 2.8 | 45.2 |
| | 1, | 20 | 4.8 | 4.1 | 46.2 |
| | 1, | 10 | 9.1 | 7.5 | 49 |
| | 1, | 4 | 20 | — | — |
| | 1, | 1 | 50 | 33.6 | 107 |
| | 10, | 1 | 91 | 55.6 | 683 |
| $(CFH = CH_2)_x/(VOH)_y$ | $x = 1,$ | $y = 40$ | 2.4 | 1.1 | 44.2 |
| | 1, | 30 | 3.2 | 1.4 | 44.6 |
| | 1, | 20 | 4.8 | 2.1 | 45.3 |
| | 1, | 10 | 9.1 | 4.0 | 47.6 |
| | 1, | 4 | 20 | — | — |
| | 1, | 1 | 50 | 21.3 | 89 |
| | 10, | 1 | 91 | 37.8 | 503 |
| $(CF_2 = CFCl)_x/(VOH)_y$ | $x = 1,$ | $y - 40$ | 2.4 | 3.1 | 46.0 |
| | 1, | 30 | 3.2 | 4.0 | 46.9 |
| | 1, | 20 | 4.8 | 5.8 | 48.9 |
| | 1, | 10 | 9.1 | 10.4 | 54.6 |
| | 1, | 4 | 20 | — | — |
| | 1, | 1 | 50 | 35.8 | 159 |
| | 10, | 1 | 91 | 47.2 | 1208 |
| $(CF_2 = CCl_2)_x/(VOH)_y$ | $x = 1,$ | $y = 40$ | 2.4 | 2.0 | 46.5 |
| | 1, | 30 | 3.2 | 2.7 | 47.7 |
| | 1, | 20 | 4.8 | 3.8 | 50.0 |
| | 1, | 10 | 9.1 | 6.7 | 57 |
| | 1, | 4 | 20 | — | — |
| | 1, | 1 | 50 | 20.8 | 183 |
| | 10, | 1 | 91 | 26.3 | 1442 |
| $(CF_2 = CFCF_3)_x/(VOH)_y$ | $x = 1,$ | $y = 40$ | 2.4 | 6.1 | 46.8 |
| | 1, | 30 | 3.2 | 7.9 | 48.0 |
| | 1, | 20 | 4.8 | 11.3 | 50.5 |
| | 1, | 10 | 9.1 | 19.6 | 58 |
| | 1, | 4 | 20 | — | — |
| | 1, | 1 | 50 | 59.0 | 193 |
| | 10, | 1 | 91 | 73.9 | 1543 |

The porous fluoropolymer membrane coated with the hydrophilic fluorine-containing copolymer may be prepared, for example, by dissolving the hydrophilic fluorine-containing copolymer in an organic solvent such as, for example, an alcohol, ketone, ester, amide or hydrocarbon, and immersing the porous fluoropolymer membrane in the resulting solution; or impregnating the membrane with the resulting solution by spraying the membrane with the resulting solution; or by coating the former with the latter by means of rolls, and drying the resulting product. This procedure may allow the hydrophilic fluorine-containing copolymer to adhere to the internal surface of the membrane, thereby enabling water to permeate through he fine pores. Although the amount of the fluorine-containing hydrophilic polymer to adhere to the substrate may vary with the porosity of the porous fluorine resin used, and so on, the amount may be in the range usually from 1.5% to 10% by weight, preferably from 2% to 6% by weight, with respect to the weight of the resulting final product.

The hydrophilic porous membrane of the present invention may also be prepared by impregnating the porous membrane with a solution of a copolymer in an organic solvent, such a copolymer being comprised of the fluorine-containing monomer with a monomer having a hydrophobic group convertible into a hydrophilic group, such as vinyl acetate, drying the substrate and converting at least a portion of the hydrophobic groups into the hydrophilic groups.

The porous fluorine resin materials according to the present invention may be in any shape such as film, seal, plate, tube, yarn, fabric, etc.

The hydrophilic porous membrane of the present invention has a structure in which the hydrophilic fluorine-containing copolymer adheres to the internal structure of the membrane that forms the pores of the membrane. The pores are thereby rendered hydrophilic so that water can permeate through the pores. Appropriate equivalent weight of copolymer, which relates to solubility of the copolymer to water, may prevent the elution of the copolymer itself from the porous material. In addition, the force by which the hydrophilic fluorine-containing copolymer is attached to and adheres to the fluoropolymer membrane is strong due tot he interaction of the fluorine atoms of the hydrophilic copolymer with those of the membrane and the durability of the copolymer can be maintained over a long period of time in a stable fashion. Hence, the present invention does not require any laborious cross-linking treatment after impregnation of the membrane with the hydrophilic fluorine-containing copolymer, as some conventional methods do.

The hydrophilic membrane of the present invention may advantageously be sued as a water permeable filter, a gas/liquid separatory membrane, an enzyme fixing membranes, and so on. The membranes of the present invention are remarkably high in heat resistance and chemical resistance because they are comprised of the fluoropolymer material as a whole.

TEST PROCEDURES

Thickness

Thickness was measured with a dial thickness gauge having an accuracy of 1/1000 of a millimeter.

Porosity

Pre-impregnation porosity is found by measuring the density of the sample. Full density of PTFE is 2.2 g/cm$^3$. The porosity is found by using the equation:

$$\text{Porosity} = \frac{2.2 - \text{density of sample}}{2.2} \times 100$$

On calculating the post-impregnation porosity the full density (2.1) of an impregnated membrane was used instead of 2.2.

Ethanol Bubble Point (EBP)

EBP was determined by spreading ethanol on the surface of the membrane specimen and placing the specimen horizontally in a clamp device. Air was blown from underneath. The EBP is the initial pressure in kg/cm$^2$ at which air bubbles appear continuously from the opposite surface.

Gurley Number (GN)

GN is determined by measuring the time required for 100 cm$^3$ air to flow through 6.45 cm$^2$ sample area under the pressure of 12.4 cm H$_2$O.

Fluorine and Hydroxyl Group Content

Fluorine content and hydroxyl group content of the copolymer were determined by calculation from the result by the elemental analysis of the copolymer.

Hydrophilicity

Initial hydrophilicity was determined by dropping a drop of water on the surface of a sheet of sample from a height of 5 cm and measuring the time it takes for the drop to be absorbed.

Degree of hydrophilicity is as follows:

A = adsorbed within 1 second
B = is eventually absorbed
C = is absorbed only by applying pressure
D = is not absorbed but contact angle becomes smaller
E = is not absorbed, i.e., it repels water. "E" is typical of porous expanded PTFE.

Flow Time

Flow time is the time required to pull 200 cc of water at 1 atmospheric vacuum through a 35 mm diameter sample. The sample was placed in a fixed horizontal position and the vacuum was pulled. Then water was poured on top. For pre-impregnation measurements the membrane was first impregnated with ethanol to make the membrane compatible with water.

Water permeability (WP)

WP was determined by the equation $$WP = \frac{200}{\text{Flow time in minutes} \times 1.75^2 \times 3.14}$$

Durability

Durability of the impregnated membrane is expressed by the Hydrophilicity after the Flow Time tests by five times with drying after each time, or after penetration with 10 liters of water using Flow Time equipment and procedure.

Heat Resistance

Heat resistance was measure by fixing the membrane on a tenter frame and then placing the material in an air oven controlled at testing temperature, for the time periods specified, followed by measuring for hydrophilicity as described above.

Resistance to Acids, Bases and Solvents

Samples were immersed in the liquid for the time and at the temperature stated in the examples. The samples were washed with water and then dried and the hydrophilicity observed according to the criteria explained below.

EXAMPLES

Example 1

A solution was prepared by dissolving a tetrafluoroethylene/vinyl alcohol copolymer (a saponified compound of a tetrafluoroethylene/vinyl acetate copolymer; saponification degree 100%, fluorine content, 27% by weight; hydroxyl group content rate, 14.5 mol/gram) in 1 liter of methanol to result in a 0.2% by weight methanol solution. A porous fluoropolymer membrane of polytetrafluoroethylene (porous expanded polytetrafluoroethylene) having a thickness of 40 microns and a porosity of 80% and an EBP of 1.2 kg/cm$^2$ was impregnated with the solution by dipping the membrane into the solution, followed by fixing the membrane on a tenter frame, followed by drying at 60° C. for 5 minutes. This operation was repeated five times, thereby producing the resulting hydrophilic porous membrane. It had a good hydrophilicity value of A and a flow time of 60 sec. (Its thickness was 30 microns; porosity, 70%; EBP, 1.2 kg/cm$^2$; pore size, 0.2 microns; WP, 20 cm$^3$/cm$^2$ min. At a heat-resistant temperature of 120° C., original good hydrophilicity remained after 24 hr.; but at 135° C., it was lost.

When the resulting membrane was immersed in water, no dissolved substances were caused to be produced in the water (i.e., no elution of copolymer), and no changes were indicated when it was immersed in boiling water. It was found that the membrane was highly resistant to acids, such as 12N-HCl at room temperature, 1N-HCl at 80° C.; and alkalis such as 5N-NaOH at room temperature, and 1N-NaOH at 80° C.

Example 2

A solution of the tetrafluoroethylene/vinyl acetate copolymer in 1 liter of methylethylketone was prepared at a 0.5% by weight concentration. This solution was used to impregnate a porous polytetrafluoroethylene membrane having a film thickness of 40 microns and a porosity of 80% and an EBP of 1.2 kg/cm$^2$, following by fixing on a tenter frame and drying at 60° C. for 5 minutes. This operation was repeated five times, and the resulting membrane was subjected to saponification by placing the resulting membrane in ethanol, adding sodium methoxide and heating for 30 minutes. The impregnated membrane was saponified and the hydrophilic membrane was washed with water. The membrane has characteristics similar to those of the film obtained in Example 1.

Comparative Example 1

A porous expanded polytetrafluoroethylene membrane having a film thickness of 40 microns, and a porosity of 80% and an EBOP of 1.2 kg/cm$^2$ was impregnated with 5% by weight of an anionic surfactant (ammonium perfluoroalkyl sulfonate), ("FC-93"; produced by 3M), as a surfactant, for 20 minutes, and the resulting membrane was dried at room temperature, thereby resulting in a hydrophilic membrane. This membrane was found so poor in durability that its hydrophilic properties were lost only when 200 ml of water had been permeated through the resulting membrane five times.

Comparative Example 2

A porous expanded polytetrafluoroethylene membrane having a film thickness of 40 microns, and a porosity of 80% and an EBP of 1.2 kg/cm$^2$, was first impregnated with isopropanol in order to make the membrane compatible with water and then immersed in a 0.1% aqueous solution of polyvinyl alcohol for 2 hours, followed by drying at 50° C. The resulting membrane had some hydrophilic properties, however, it was found that its hydrophilic properties were gradually decreased and totally lost in 24 hours, when immersed in 3N HCl. When it was immersed in 5N HCl, the resulting membrane has lost its hydrophilic properties in 12 hours. Its heat resistant temperature was only 110° C.

Thus, the impregnated membranes of this invention are superior to this polyvinyl alcohol impregnated membrane in thermal stability, stability in acids or bases, and in durability.

Example 3

A porous PTFE membrane having a thickness of 48 um, a GN of 6.1 seconds, a EBP of 1.15 kg/cm$^2$, a porosity of 76% and flow time of 36 seconds was impregnated with a 1% methanol solution of the copolymer used in Example 1. The membrane was immersed in the solution for 30 seconds, taken out, set in a tenter frame and dried for 1 hour at room temperature.

The properties of the impregnated membrane were: amount of copolymer in membrane, 0.75 g/m$^2$; thickness 39 um; GN 10.4 seconds; EBP 1.2 kg/cm$^2$; porosity 71%; flow time 56 seconds (speed of WP, 20 cm$^3$/cm$^2$.min.).

The impregnated membrane was penetrated five times with 200 ml of water with drying after each time, or was continuously penetrated with 10 liters of water and the hydrophilicity test was then carried out with the following results:

| DURABILITY TEST CONDITION | HYDROPHILICITY TEST RESULTS |
|---|---|
| Penetration 5 times with 200 ml of water with drying after each time | A |
| Penetration continuously with 10 liters of water | A |

The impregnated membrane was subject to the Flow Time test five (5) times with drying after each time. Then, the membrane was given the Hydrophilicity test. It tested A.

Another sample of the impregnated membrane was continuously penetrated with 10 liters of water using the Flow Time equipment and procedure, then it was treated for hydrophilicity. It measured A.

Another sample of the impregnated membrane was heated at the following temperatures for the following times and the hydrophilicity test was then carried out with the following results:

| TEMPERATURE | TIME | HYDROPHILICITY TEST RESULT |
|---|---|---|
| 100° C. | 30 hr. | A |
| 120° C. | 6 hr. | B (absorbed after 60 sec) |
| 120° C. | 24 hr. | B (absorbed after 60 sec) |
| 120° C. | 48 hr. | B (absorbed after 120 sec) |
| 150° C. | 2 hr. | C or D |
| 150° C. | 24 hr. | D |
| 200° C. | 1 hr. | D |

Another sample of the impregnated membrane was immersed under the following oxidative conditions for the following times and the hydrophilicity test was then carried out with the following results:

| OXIDATIVE AGENT | TEMPERATURE | TIME | HYDROPHILICITY TEST RESULTS |
|---|---|---|---|
| 2N-HNO$_3$ | 85° C. | 2 hr. | A |
| 3N-HNO$_3$ | R.T. | 350 hr. | A |

Hydrophilicity after immersion for 350 hours in 3N-HNO$_3$ at room temperature was: A.

Hydrophilicity after immersion for 2 hours in 2N-HNO$_3$ at 85° C. was: A.

Another sample of the impregnated membrane was immersed under the following acidic conditions for the following time and the hydrophilicity test was then carried out with the following results:

| ACIDIC AGENT | TEMPERATURE | TIME | HYDROPHILICITY TEST RESULTS |
|---|---|---|---|
| 1N-HCl | 80° C. | 1 hr. | A |
| 3N-HCl | R.T. | 350 hr. | A |
| 12N-HCl | R.T. | 1 hr. | A |

Resistance to Alkali

Another sample of the impregnated membrane was immersed under the following basic conditions for the following time and the hydrophilicity test was then carried out with the following results:

| BASIC AGENT | TEMPERATURE | TIME | HYDROPHILICITY TEST RESULTS |
|---|---|---|---|
| 1N-NaOH | 80° C. | 1 hr. | A |
| 1N-NaOH | 80° C. | 5 hr. | D |
| 6N-NaOH | R.T. | 36 hr. | A |

Another sample of the impregnated membrane was penetrated with solvents under the following conditions and the hydrophilicity test was then carried out with the following results:

| ORGANIC SOLVENT | PENETRATION VOLUME | HYDROPHILICITY TEST RESULTS |
|---|---|---|
| Methanol | 300 ml | A |
| Ethanol | 2000 ml | A |
| Acetone | 5000 ml | A |

We claim:

1. A hydrophilic porous membrane comprising a polytetrafluoroethylene membrane having continuous pores through the membrane, in which at least a portion of the interior of the membrane is coated with a hydrophilic fluorine-containing copolymer comprising (i) units of a fluorine-containing monomer and (ii) units of a non-fluorinated vinyl monomer containing a hydrophilic functional group; wherein the amount of the copolymer present is sufficient to impart increased hydrophilicity to the fluoropolymer membrane in order to permit penetration of water therethrough.

2. The hydrophilic porous membrane of claim 1 wherein the polytetrafluoroethylene is expanded polytetrafluoroethylene.

3. The hydrophilic membrane of claim 1 or 2 wherein the fluorine content of the hydrophilic fluorine-containing polymer is between 2 and 60 percent by weight of the copolymer and wherein the ratio of the formula weight of the recurring units of the copolymer to the number of functional group is the formula is between 45 and 700.

4. The hydrophilic copolymer of claim 3 wherein the ratio of the formula weight of the recurring units of the copolymer to the number of functional group in the formula is between 60 and 500.

5. The hydrophilic porous membrane of claim 1 wherein in the hydrophilic fluorine-containing copolymer the units of the fluorine-containing monomer are units of an ethylenically unsaturated vinyl monomer.

6. The hydrophilic porous membrane of claim 5 wherein the porous fluoropolymer membrane is polytetrafluoroethylene.

7. The hydrophilic porous membrane of claim 6 wherein the polytetrafluoroethylene is expanded polytetrafluoroethylene.

8. The hydrophilic membrane of claim s 5, 6 or 7 wherein the fluorine content of the hydrophilic fluorine-containing polymer is between 2 and 60 percent by weight of the copolymer, and wherein the ratio of the formula weight of the recurring units of the copolymer to the number of functional group is the formula is between 45 and 700.

9. The hydrophilic copolymer of claim 8 wherein the ratio of the formula weight of the recurring units of the copolymer to the number of functional group in the formula is between 60 and 500.

10. The hydrophilic porous membrane of claim 1 wherein the units of the vinyl monomer are selected from the class consisting of vinylidene fluoride, vinyl fluoride, monochlorotrifluoroethylene, dichlorodifluoroethylene, hexafluoropropene and tetrafluoroethylene.

11. The hydrophilic porous membrane of claim 10 wherein the porous fluoropolymer membrane is polytetrafluoroethylene.

12. The hydrophilic porous membrane of claim 11 wherein the polytetrafluoroethylene is expanded polytetrafluoroethylene.

13. The hydrophilic membrane of claim 11 or 12 wherein the fluorine content of the hydrophilic fluorine-containing polymer is between 2 and 60 percent by weight of the copolymer, and wherein the ratio of the formula weight of the recurring units of the copolymer to the number of functional group is the formula is between 45 and 700.

14. The hydrophilic copolymer of claim 13 wherein the ratio of the formula weight of the recurring units of the copolymer to the number of functional group in the formula is between 60 and 500.

15. The hydrophilic porous membrane of claim 1 wherein in the hydrophilic fluorine-containing copolymer the functional group of the units of vinyl monomer containing a hydrophilic functional group are selected from the class consisting of hydroxyl group, carboxyl group, sulfonic group, amide, —COOHN$_2$ and amine.

16. The hydrophilic porous membrane of claim 15 wherein the porous fluoropolymer membrane is polytetrafluoroethylene.

17. The hydrophilic porous membrane of claim 16 wherein the polytetrafluoroethylene is expanded polytetrafluoroethylene.

18. The hydrophilic membrane of claim 15, 16 or 17 wherein the fluorine content of the hydrophilic fluorine-containing polymer is between 2 and 60 percent by weight of the copolymer, and wherein the ratio of the formula weight of the recurring units for the copolymer to the number of functional group is the formula is between 45 and 700.

19. The hydrophilic copolymer of claim 18 wherein the ratio of the formula weight of the recurring units of the copolymer to the number of functional group in the formula is between 60 and 500.

20. The hydrophilic porous membrane of claim 1 wherein, in the hydrophilic fluorine-containing copolymer the units of fluorine-containing monomer are selected from the class consisting of vinylidene fluoride, vinyl fluoride, monochlorotrifluoroethylene, dichlorodifluoroethylene, hexafluoropropylene and tetrafluoroethylene, and the functional group of the units of vinyl monomer containing a hydrophilic function group are selected from the class consisting of hydroxyl group, carboxyl group, sulfonic group, amide, —COONH$_2$ and amine.

21. The hydrophilic porous membrane of claim 20 wherein the porous fluoropolymer membrane is polytetrafluoroethylene.

22. The hydrophilic porous membrane of claim 21 wherein the polytetrafluoroethylene is expanded polytetrafluoroethylene.

23. The hydrophilic membrane of claim 20, 21 or 22 wherein the fluorine content of the hydrophilic fluorine-containing polymer is between 2 and 60 percent by weight of the copolymer, and wherein the ratio of the formula weight of the recurring units of the copolymer to the number of functional groups in the formula is between 45 and 700.

24. The hydrophilic copolymer of claim 23 wherein the ratio of the formula weight of the recurring units of the copolymer to the number of functional group in the formula is between 60 and 500.

25. The hydrophilic porous membrane of claim 1 wherein in the hydrophilic fluorine-containing copolymer, the units of fluorine-containing monomer are tetrafluoroethylene units and the units of vinyl monomer containing a hydrophilic group are units of vinyl alcohol.

26. The hydrophilic porous membrane of claim 25 wherein the porous fluoropolymer membrane is polytetrafluoroethylene.

27. The hydrophilic porous membrane of claim 26 wherein the polytetrafluoroethylene is expanded polytetrafluoroethylene.

28. The hydrophilic membrane of claim 25, 26 or 27 wherein the fluorine content of the hydrophilic fluorine-containing polymer is between 2 and 60 percent by weight of the copolymer, and wherein the ratio of the formula weight of the recurring units of the copolymer to the number of functional group is the formula is between 45 and 700.

29. The hydrophilic copolymer of claim 28 wherein the ratio of the formula weight of the recurring units of the copolymer to the number of functional group in the formula is between 60 and 500.

* * * * *